(12) United States Patent
Altmann

(10) Patent No.: US 11,471,219 B2
(45) Date of Patent: Oct. 18, 2022

(54) CATHETER PROBE NAVIGATION METHOD AND DEVICE EMPLOYING OPPOSING TRANSDUCERS

(71) Applicant: Biosense Webster (Israel) Ltd., Yokneam (IL)

(72) Inventor: Andres Claudio Altmann, Haifa (IL)

(73) Assignee: BIOSENSE WEBSTER (ISRAEL) LTD., Yokneam (IL)

( * ) Notice: Subject to any disclaimer, the term of this patent is extended or adjusted under 35 U.S.C. 154(b) by 541 days.

(21) Appl. No.: 15/680,292

(22) Filed: Aug. 18, 2017

(65) Prior Publication Data

US 2019/0053854 A1 Feb. 21, 2019

(51) Int. Cl.
*A61B 34/20* (2016.01)
*A61B 18/00* (2006.01)
(Continued)

(52) U.S. Cl.
CPC ............ *A61B 34/20* (2016.02); *A61B 5/6853* (2013.01); *A61M 25/00* (2013.01); *A61N 1/05* (2013.01);
(Continued)

(58) Field of Classification Search
CPC ............ A61B 34/20; A61B 2034/2063; A61B 2034/2051; A61B 5/042; A61B 5/063; A61B 18/1492; A61B 2018/0022; A61B 2018/00351; A61B 2018/00577; A61B 8/12; A61B 8/4245; A61B 8/4254; A61B 8/44
See application file for complete search history.

(56) References Cited

U.S. PATENT DOCUMENTS

| 5,391,199 A | 2/1995 | Ben-Haim |
| 5,443,489 A | 8/1995 | Ben-Haim |

(Continued)

FOREIGN PATENT DOCUMENTS

| WO | 2012/122517 A2 | 9/2012 |
| WO | 2014/124231 A1 | 8/2014 |

(Continued)

OTHER PUBLICATIONS

Goldberg, Richard L., Stephen W. Smith, and Lewis F. Brown. "In vivo imaging using a copolymer phased array." Ultrasonic imaging 14, No. 3 (1992): 234-248.*
(Continued)

*Primary Examiner* — Carolyn A Pehlke
(74) *Attorney, Agent, or Firm* — Volpe Koenig

(57) ABSTRACT

A probe navigation methods and devices for use in medical diagnoses and procedures are provided. A probe that is inserted in a walled area within a subject has a distal end on which at least first and second opposing transducers are mounted. The transducers track movement of the probe end with respect to the walls of the walled area. The distal end of the probe may closely approach a wall to enter an area such that the first transducer is no longer able to properly sense it, commonly referred to as a blanking region. Tracking information of the movement of the probe away from an opposing wall generated by the second transducer is then used to provide tracking of the distal end of the probe relative to the wall the first transducer is no longer able to sense.

20 Claims, 4 Drawing Sheets

(51) Int. Cl.
  *A61N 1/05* (2006.01)
  *A61M 25/00* (2006.01)
  *A61B 5/00* (2006.01)
  *A61B 5/283* (2021.01)
  *A61B 90/00* (2016.01)
  *A61B 5/06* (2006.01)
  *A61B 18/14* (2006.01)

(52) U.S. Cl.
  CPC ............... *A61B 5/063* (2013.01); *A61B 5/283* (2021.01); *A61B 18/1492* (2013.01); *A61B 2018/0022* (2013.01); *A61B 2018/00351* (2013.01); *A61B 2018/00577* (2013.01); *A61B 2034/2051* (2016.02); *A61B 2034/2063* (2016.02); *A61B 2090/061* (2016.02)

(56) References Cited

U.S. PATENT DOCUMENTS

| | | | |
|---|---|---|---|
| 5,558,091 A | 9/1996 | Acker | |
| 5,590,659 A | 1/1997 | Hamilton | |
| 5,865,801 A * | 2/1999 | Houser | A61B 5/036 600/488 |
| 5,944,022 A | 8/1999 | Nardella | |
| 5,983,126 A | 11/1999 | Wittkampf | |
| 6,172,499 B1 | 1/2001 | Ashe | |
| 6,177,792 B1 | 1/2001 | Govari | |
| 6,266,551 B1 | 7/2001 | Osadchy | |
| 6,445,944 B1 | 9/2002 | Ostrovsky | |
| 6,547,788 B1 * | 4/2003 | Maguire | A61B 18/00 606/41 |
| 6,690,963 B2 | 2/2004 | Ben-Haim | |
| 6,788,967 B2 | 9/2004 | Ben-Haim | |
| 7,291,110 B2 * | 11/2007 | Sahatjian | A61B 5/02007 600/439 |
| 2006/0253028 A1 * | 11/2006 | Lam | A61B 8/12 600/459 |
| 2009/0093806 A1 | 4/2009 | Govari | |
| 2009/0138007 A1 | 5/2009 | Govari | |
| 2010/0076299 A1 * | 3/2010 | Gustus | A61B 5/0084 600/411 |
| 2016/0051321 A1 * | 2/2016 | Salahieh | A61B 1/00082 600/439 |

FOREIGN PATENT DOCUMENTS

| | | |
|---|---|---|
| WO | 2014/188430 A2 | 11/2014 |
| WO | 2015/148470 A1 | 10/2015 |
| WO | 2016/183285 A1 | 11/2016 |

OTHER PUBLICATIONS

International Search Report and Written Opinion of the International Searching Authority for PCT International Application No. PCT/IB2018/056118 dated Dec. 7, 2018.

* cited by examiner

CATHETER PROBE NAVIGATION METHOD AND DEVICE EMPLOYING OPPOSING TRANSDUCERS

SUMMARY

A probe navigation method and device are provided for use in medical diagnostic and other procedures in walled cavities and passages of a subject. Opposing transducers are employed to compensate for signal blanking regions resulting from close proximity of sensors relative to walls within which the probe, such as a catheter, is positioned.

In one embodiment, a probe that has a distal end of on which first and second opposing transducers are mounted is inserted in a walled area within a subject. The transducers track movement of the probe end with respect to the walls of the walled area. The distal end of the probe may closely approach a wall to enter an area such that the first transducer is no longer able to properly sense it. Such an area is commonly referred to as a blanking region. Tracking information of the movement of the probe away from an opposing wall generated by the second transducer is then used to provide tracking of the distal end of the probe relative to the wall the first transducer is no longer able to sense. Accordingly, contact with the wall is determinable irrespective of the inability of the first transducer to properly sense it.

The method may be performed such that the probe is a catheter and the distal end of the catheter is positioned within a heart chamber of a living subject. The catheter can include a sheath through which tools are deployed wherein a distal end of the catheter sheath includes a balloon having first and second transducers mounted thereon. An alternative embodiment may have opposing transducers mounted directly on the tool deployed through the sheath and/or balloon. In each aforementioned example, the opposing transducers may be mounted on the distal end of the probe at, for example, an angle of 180 degrees from each other with respect to an axis of the probe. However, other angular orientations may be used.

The distal end of the probe can be configured to include more than two transducers, such as with a balloon with an array of transducer supporting members where each supporting member includes a plurality of transducer elements. Where the distal end of such a probe enters a blanking region with respect to a particular transducer, tracking information generated from multiple other transducers can be used to track the probe's movement towards the wall after it enters the blanking region of the particular transducer.

The positioning and/or tracking information of the distal end of a catheter or the like according to the above methods can be displayed, graphically or otherwise, on a display. A physician or other probe operator can then position the distal end of the probe based on the displayed information.

An example probe navigation device utilizing the methodologies above within a subject may include: a control system and associated probe with distal end comprised of any of the aforementioned variations, configured to be controllably inserted and moved within a walled area of the subject. The example control system is configured to track movement of the distal end of the probe towards a first wall using a first transducer and with respect to other wall portions, such as away from an opposing wall, using one or more other transducers. Upon a condition that the distal end of the probe closely approaches the first wall where the first transducer is unable to properly sense the first wall, the control system is configured to use information generated by the one or more other transducers of the movement of the probe with respect to the walls of the walled area, such as away from the opposing wall, to provide tracking of the distal end of the probe towards the first wall. This enables contact with the first wall to be determinable irrespective of the inability of the first transducer to properly sense the first wall.

Such a control system can include a processor coupled with the transducers and configured to calculate the tracking information of the probe movement based on transducer signals, a display coupled with the processor configured to display the tracking information in one or more modes, and an operable probe control device configured to be operated to selectively control the positioning of the distal end of the probe based on the displayed tracking information.

Other object and advantages of the invention will be apparent to those skilled in the art from the drawings and following detailed description.

BRIEF DESCRIPTION OF THE DRAWINGS

The present embodiments are illustrated by way of example, and not by way of limitation, in the figures of the accompanying drawings.

DETAILED DESCRIPTION OF THE EMBODIMENTS

Documents incorporated by reference in the present patent application may include terms that are defined in a manner that conflicts with the definitions made explicitly or implicitly in the present specification. In the event of any conflicts, the definitions in the present specification should be considered to be controlling.

Figure 1:
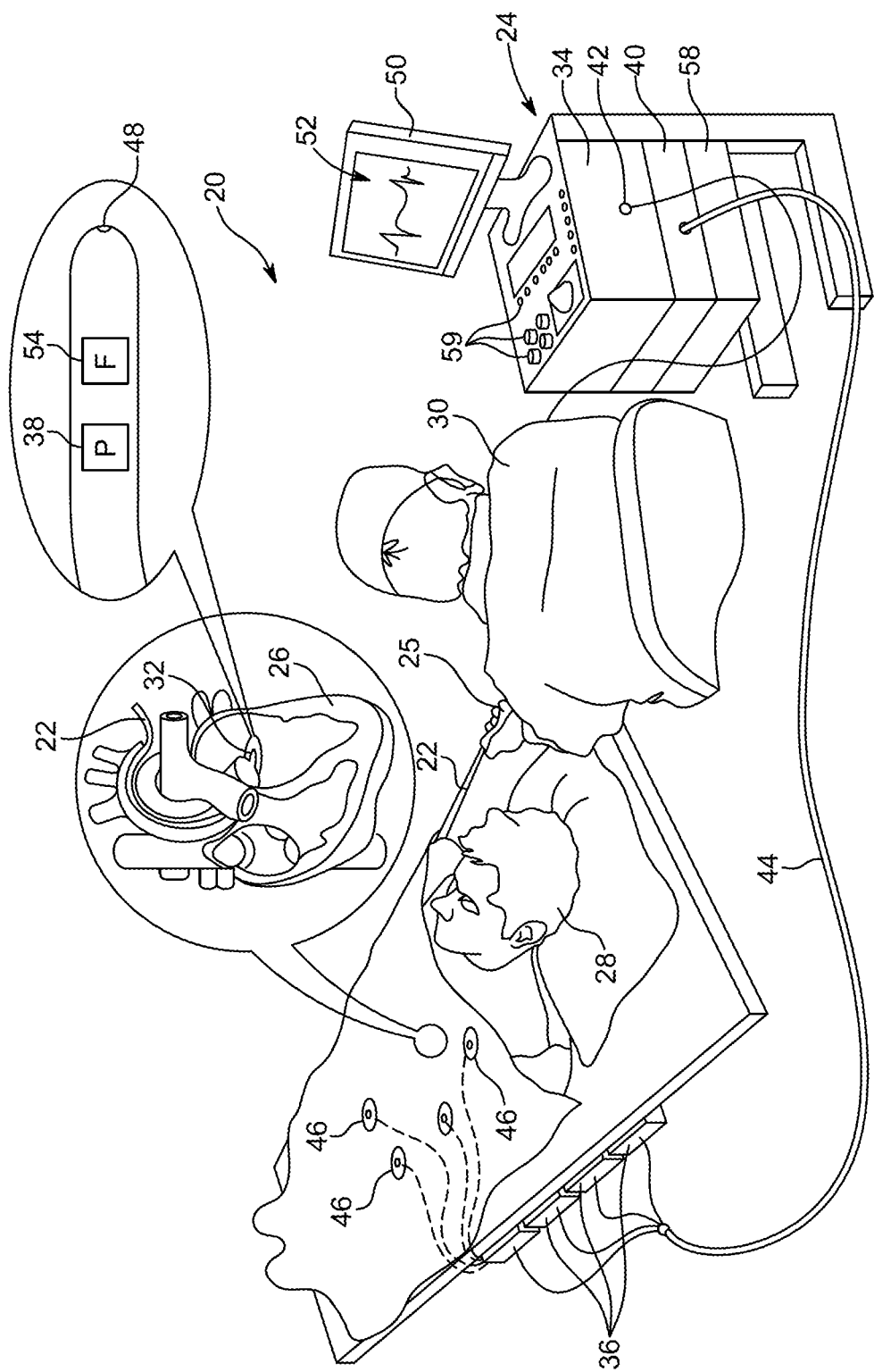
FIG. 1 is an example schematic, pictorial illustration of a medical system for conducting mapping, diagnostic and other procedures in accordance with the teachings of the present invention.

FIG. 1 is an illustration of an example medical system 20 that is used to generate and display information 52 during a mapping, diagnostic or other medical procedure and to control the deployment of various probes within a subject. The example system includes a probe 22, such as an intracardiac catheter, a console 24 and an associated probe control unit 25. As described herein, it will be understood that the probe 22 is used for diagnostic or therapeutic treatment, such as for example, mapping electrical potentials in a heart 26 of a patient 28 or performing an ablation procedure. Alternatively, the probe 22 can be used, mutatis mutandis, for other therapeutic and/or diagnostic purposes in the heart, lungs, or in other body organs and ear, nose, and throat (ENT) procedures.

An operator 30 can, for example, insert the probe 22 into the vascular system of the patient 28 using the probe control unit so that a distal end 32 of the probe 22 enters a chamber of the patient's heart 26. The console 24 can use magnetic position sensing to determine position coordinates of the distal end 32 inside the heart 26. To determine the position coordinates, a driver circuit 34 in the console 24 may drive field generators 36 to generate magnetic fields within the body of the patient 28. The field generators 36 can include coils that may be placed below the torso of the patient 28 at known positions external to the patient 28. These coils may generate magnetic fields in a predefined working volume that contains the heart 26.

A position sensor 38 within the distal end 32 of the probe 22 can generate electrical signals in response to these magnetic fields. A signal processor 40 can process these signals in order to determine the position coordinates of the distal end 32, including both location and orientation coordinates. Known methods of position sensing described hereinabove are implemented in the CARTO™ mapping system produced by Biosense Webster Inc., of Diamond Bar, Calif., and is described in detail in the patents and the patent applications cited herein.

The position sensor 38 is configured to transmit a signal to the console 24 that is indicative of the location coordinates of the distal end 32. The position sensor 38 can include one or more miniature coils, and typically can include multiple coils oriented along different axes. Alternatively, the position sensor 38 can comprise either another type of magnetic sensor, or position transducers of other types, such as impedance-based or ultrasonic position sensors. As described in more detail below, the position sensor 38 can include one or more sets of opposing transducers.

The probe 22 can also include a force sensor 54 contained within the distal end 32. The force sensor 54 can measure a force applied by the distal end 32 to the endocardial tissue of the heart 26 and generating a signal that is sent to the console 24. The force sensor 54 can include a magnetic field transmitter and a receiver connected by a spring in the distal end 32, and can generate an indication of the force based on measuring a deflection of the spring. Further details of this type of probe and force sensor are described in U.S. Patent Application Publications 2009/0093806 and 2009/0138007, and are incorporated herein by reference as if fully set forth. Alternatively, the distal end 32 can include another type of force sensor that can use, for example, fiber optics or impedance measurements.

The probe 22 can include an electrode 48 coupled to the distal end 32 and configured to function as an impedance-based position transducer. Additionally or alternatively, the electrode 48 can be configured to measure a certain physiological property, for example the local surface electrical potential of the cardiac tissue at one or more of the multiple locations. The electrode 48 can be configured to apply radio frequency (RF) energy to ablate endocardial tissue in the heart 26.

Although the example medical system 20 can be configured to measure the position of the distal end 32 using magnetic-based sensors, other position tracking techniques can be used (e.g., impedance-based sensors). Magnetic position tracking techniques are described, for example, in U.S. Pat. Nos. 5,391,199, 5,443,489, 6,788,967, 6,690,963, 5,558,091, 6,172,499, and 6,177,792, and are incorporated herein by reference as if fully set forth. Impedance-based position tracking techniques are described, for example, in U.S. Pat. Nos. 5,983,126 and 5,944,022, and are incorporated herein by reference as if fully set forth.

The signal processor 40 can be included in a general-purpose computer with a suitable front end and interface circuits for receiving signals from the probe 22 and controlling the other components of the console 24. The signal processor 40 can be programmed, using software, to carry out the functions that are described herein. The software can be downloaded to the console 24 in electronic form, over a network, for example, or it can be provided on non-transitory tangible media, such as optical, magnetic or electronic memory media. Alternatively, some or all of the functions of the signal processor 40 can be performed by dedicated or programmable digital hardware components.

In the example of FIG. 1, the console 24 can also be connected by a cable 44 to external sensors 46. The external sensors 46 can include body surface electrodes and/or position sensors that can be attached to the patient's skin using, for example, adhesive patches. The body surface electrodes can detect electrical impulses generated by the polarization and depolarization of cardiac tissue. The position sensors can use advanced catheter location and/or magnetic position sensors to locate the probe 22 during use. Although not shown in FIG. 1, the external sensors 46 can be embedded in a vest that is configured to be worn by the patient 28. The external sensors 46 can aid in identifying and tracking the respiration cycle of the patient 28. The external sensors 46 can transmit information to the console 24 via the cable 44.

Additionally, or alternatively, the probe 22, and the external sensors 46 can communicate with the console 24 and one another via a wireless interface. For example, U.S. Pat. No. 6,266,551, whose disclosure is incorporated herein by reference, describes, inter alia, a wireless catheter, which is not physically connected to signal processing and/or computing apparatus. Rather, a transmitter/receiver is attached to the proximal end of the catheter. The transmitter/receiver communicates with a signal processing and/or computer apparatus using wireless communication methods, such as infrared (IR), radio frequency (RF), wireless, Bluetooth®, acoustic or other transmissions.

The probe 22 can be equipped with a wireless digital interface that can communicate with a corresponding input/output (I/O) interface 42 in the console 24. The wireless digital interface and the I/O interface 42 can operate in accordance with any suitable wireless communication standard that is known in the art, such as IR, RF, Bluetooth, one of the IEEE 802.11 families of standards, or the HiperLAN standard. The external sensors 46 can include one or more wireless sensor nodes integrated on a flexible substrate. The one or more wireless sensor nodes can include a wireless transmit/receive unit (WTRU) enabling local digital signal processing, a radio link, and a power supply such as miniaturized rechargeable battery.

The I/O interface 42 can enable the console 24 to interact with the probe 22 and the external sensors 46. Based on the electrical impulses received from the external sensors 46 and signals received from the probe 22 via the I/O interface 42 and other components of the medical system 20, the signal processor 40 can generate the information 52, which can be shown on a display 50. The information 52 can be represented in the form of data or graphic interpretation such as, for example, a chart, a photograph, video or other type of graphic display.

During the diagnostic treatment, the signal processor 40 can present the information 52 and/or can store data representing the information 52 in a memory 58. The memory 58 can include any suitable volatile and/or non-volatile memory, such as random access memory or a hard disk drive.

The probe control unit 25 can be configured to be operated by an operator 30 to manipulate the probe based on the information 52 which is selectable using one or more input devices 59. Alternatively, the medical system 20 can include a second operator that manipulates the console 24 while the operator 30 operates the probe control unit 25 to manipulate the probe 22 based on the displayed information 52.

One option for treating cardiac arrhythmias can be an interventional catheter based procedure. An interventional catheter based procedure can involve a technique referred to as cardiac ablation. In such a procedure, a catheter is usually advanced from the groin area of a patient into the heart. Once in place, radio frequency (RF) energy can be delivered through the catheter to a specific location within a chamber of the subject's heart with the goal of re-establishing proper heart conduction.

During such a medical procedure proper positioning of the distal end of the catheter is of critical importance so that a precise application of radio frequency (RF) energy is delivered to the specified location or series of locations, as determined by diagnostics. Precise positioning of the probe is also important in diagnostic and mapping procedures that are performed in advance of such a medical procedure to determine the specific area of the heart requiring treatment.

The mechanics of the construction and use of the probe control device 25 to move and position the distal end of a probe is within the state of the art such as employed in the CARTO™ mapping system referenced above. For example, see also U.S. Pat. No. 6,690,963 which is incorporated herein by reference as if fully set forth. However, the operation of the probe control device 25 to control the movement of the distal end of the probe is dependent on obtaining accurate and precise data of its movement and position.

On-probe sensors such as ultra sound transducers are capable of very precise sensing of the relative location of the walls of organs, vessels and other tissues to provide very precise positioning data of a probe. When using ultrasound transducers for determining the position data, a small "dead zone" is typically produced just in front of the transducer within which the sensor cannot properly operate.

For example, an ultrasound transducer can transmit a pulse of sound and then listen for a returning sound, i.e. echo. The sensor detects the echo and associates the echo with the surface of the target. The amount of time between the initial pulse and the returning echo is used to calculate the distance between the transducer and the target surface. By repeating the pulsing during movement, tracking data can be generated with respect to the transducer and an object in front of it, such as the wall of an organ or vessel, using the determined distances calculated from the returning echoes. As well known in the art, speed is also readily calculated from returning echoes when transmitting pulses at regular time intervals of a known frequency. Calculations derived from speed and distance data are then used to track relative movement of the transducer and, accordingly, the distal probe end, to which it is attached.

Since a transducer both transmits and receives pulses, when a reflective object is too close to the transducer, it sometimes can mistake its own pulse (i.e., the vibration from its own pulse) for a returning signal. As a solution, the sensor on the transducer can be configured to ignore the vibration from all pulses as long as necessary for the vibration to stop so that is does not sense its transmitted pulse directly. As a consequence, the transducer also ignores the echo signal from a close object. For example, a catheter's transducer may be moved too close to the wall of a heart chamber for the transducer to properly sense it since the transducer begins to ignore signals bouncing off that wall.

The distance a pulse travels during the time the transducer transmits a pulse and can reliably sense an echo thereof can be referred to as a blanking distance or a dead zone. The blanking distance becomes an issue when a transducer is used to measure objects within a very close distance, for example, less than a half millimeter, in the context of transducers of the type used with a medical probe.

Figure 2:
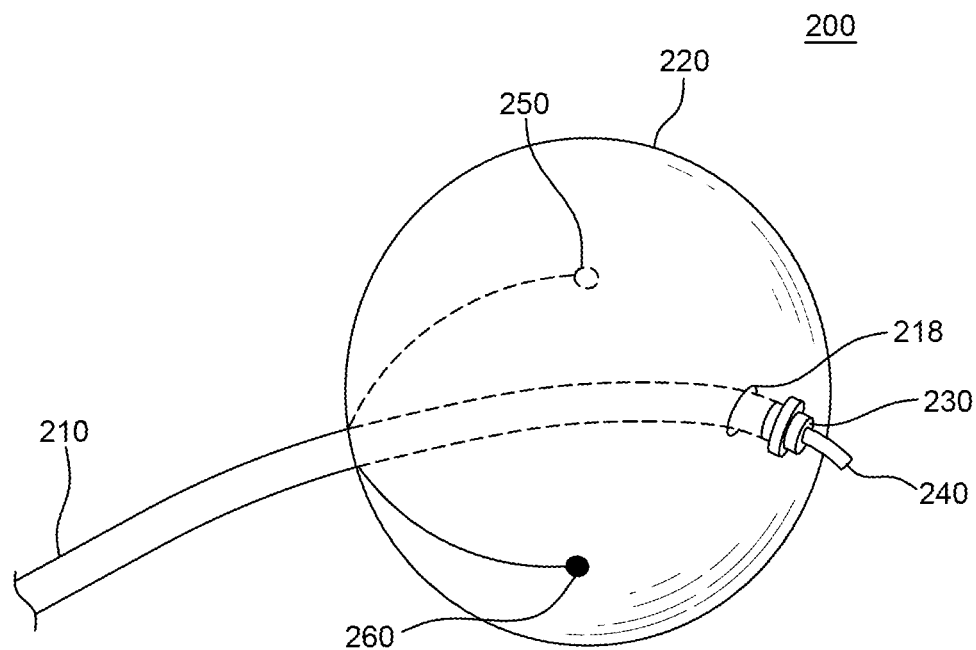
FIG. 2 is an example balloon configuration with opposing transducers for the distal end of a catheter used in connection with the example medical system of FIG. 1.

FIG. 2 provides an example of use of a set of opposing transducers that are able to compensate for the blanking region of either. FIG. 2 illustrates an example configuration of a distal end portion 200 for the probe 22 of FIG. 1. In this example, a balloon 220 is attached at a predetermined location to a probe sheath 210. The sheath 210 traverses through the balloon 220 from an opening on a proximal end and, in this example, exits the balloon 220 from an opening 218 on a distal end. The sheath 210 terminates in an end 230 from which a tool 240 or other device can extend.

In this example, the balloon 220 includes a first transducer 250 mounted on one side of the balloon 220 and a second transducer 260 mounted on an opposing side. In order to differentiate the signals (i.e., pulses) transmitted from each transducer, the first transducer 250 can transmit a signal at a first frequency, and the second transducer 260 can transmit a signal at a second, different frequency. Other differentiation techniques known in the art can be employed alone or in combination with frequency differentiation.

Figure 3A:
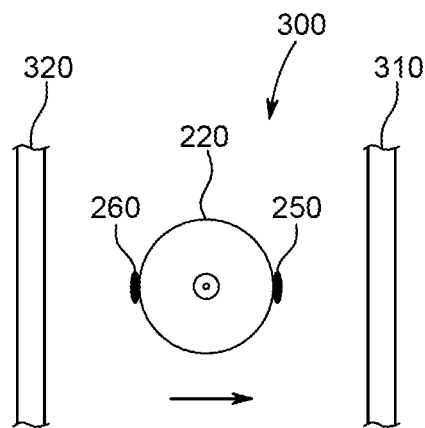
FIGS. 3A-C is a series of diagrams illustrating a method of utilizing the example balloon configuration of FIG. 2.
Figure 3B:
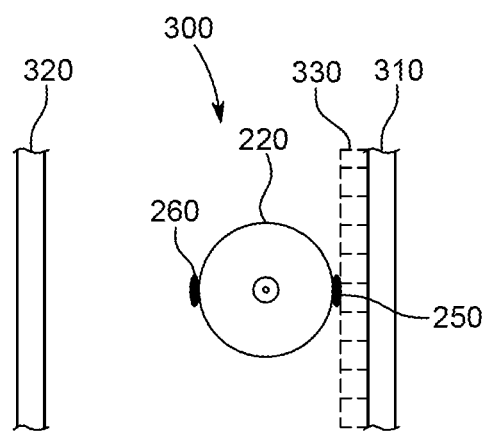
Figure 3C:
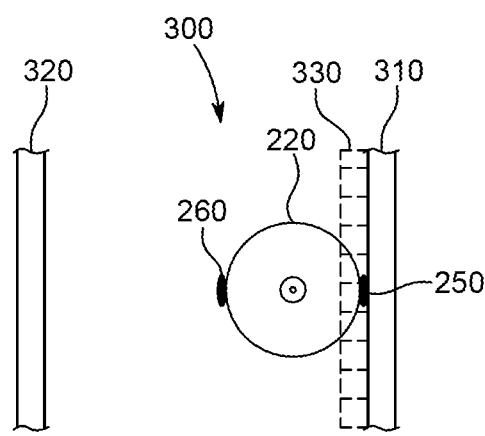

With reference to FIGS. 3A-C, the example probe end portion 200 is shown positioned in a walled area 300 of a subject having a first wall 310 and an opposing wall 320. In FIG. 3A, the balloon 220 is positioned at a position far enough away from both the walls 310, 320 such that the first transducer can sense the first wall 310 and the opposing transducer 260 can sense the opposing wall 320. Signals from both transducers are used for providing the information to the signal processor 40 (FIG. 1) which in turn provides the probe operator 30 position data 52 on the display 50 in a desired format, which may include a split screen of graphics and distance/tracking data generated from the transducer signals.

As the operator uses the probe control device 25 to move the distal end portion 200 of the probe 22 in the direction indicated by an arrow in FIG. 3A, towards the first wall 310, the processor can use additional signals from both transducers 250, 260 to change the probe position displayed on the display 50 to reflect the changed probe position, as well as tracking data that can include speed and a motion vector.

The changes in position display and tracking data can be generated using both transducers to provide very precise information regarding the movement of the balloon 220 and accordingly, the distal end of the probe 22, until the balloon enters a blanking region 330 relative to the first transducer 250. The blanking region is defined by a distance in front of the first transducer 250 within which the first transducer in unable to properly operate to sense the distance of the wall 310 directly in front of it. At that point, the opposing transducer is still able to provide position and tracking data with respect to the opposing wall 320 and that information can be used to continue an accurate display of the movement of the balloon as it travels the short distance through the blanking area to enable the operator to control the balloon to a precise position in contact with the wall 310 illustrated in FIG. 3C.

When using a balloon, such as balloon 220, typically the probe is initially inserted into a subject in a deflated orientation. When the distal end of the probe is positioned within a desired walled cavity, the balloon is then expanded. If the balloon is not expanded to a precise degree, there may be deviation in the expected distance between the first and second transducers 250 and 260. Such distance is an additional factor that can be used in generating precise position and movement tracking information regarding the movement of the balloon.

The first transducer 250 can receive a signal from the second transducer 260 and/or an echo signal reflected from a target surface but originating as a pulse from the second transducer 260. In addition, the second transducer 260 can receive a signal from the first transducer 250 and/or a signal reflected from a target surface but originating as a pulse from the first transducer 250. The system can use the received signals and/or echoes to correlate the precise distance between the first transducer 250 and the second transducer 260.

Figure 4:
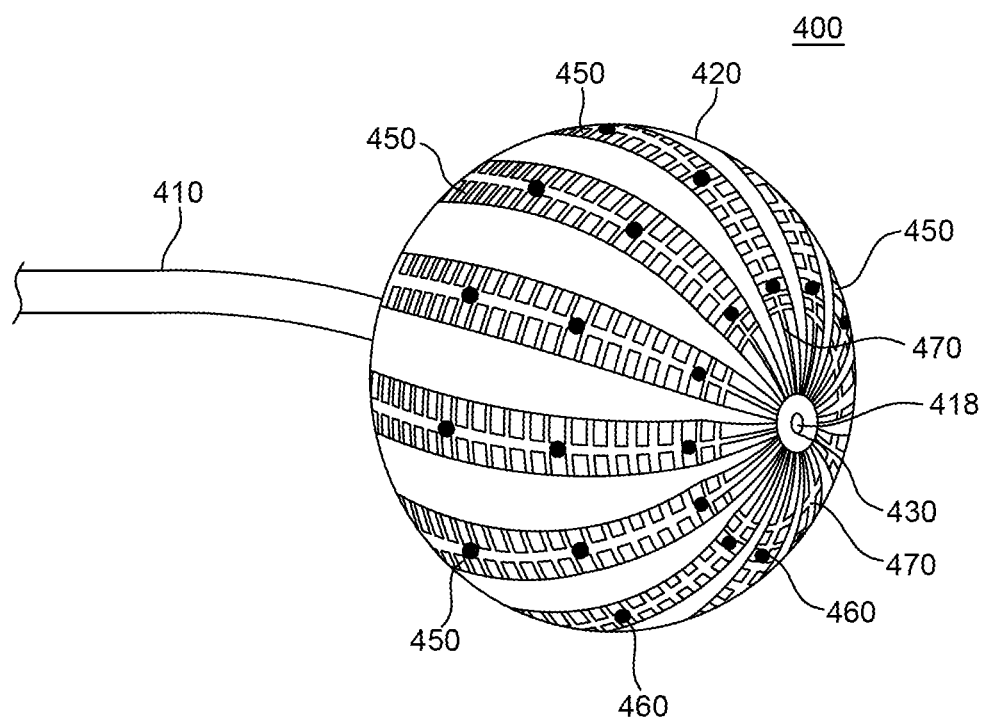
FIG. 4 is an alternative example balloon configuration for the distal end of a catheter used in connection with the example medical system of FIG. 1.

FIG. 4 is an illustration of a further example of a distal end portion 400 of the probe 22 employing opposing transducers. In this example, a balloon 420 is attached at a predetermined location to a probe sheath 410. The sheath 410 traverses through the balloon 420 from an opening on a proximal end of the balloon 420 and terminates at the opposite side of the balloon 420 at an opening 418 on a distal end. The sheath 410 includes an opening 430 from which a tool or other device, not shown, can extend.

In this example, the balloon 420 includes an array of transducer supporting members 450, each including a plurality of transducer elements 460. Each supporting member 450 is associated with a second supporting member to define a complementary pair 470 of supporting members 450 that are preferably, though not exclusively, 180 degrees opposite from one another. The transducers 460 are configured to sense different portions of walls of a walled cavity into which the distal end of the probe is located.

Each transducer element 460 on each supporting member 450 can be paired with a transducer on the complementary supporting member 450 of a supporting member pair 470 to define sets of transducer elements 460 opposite each other on the surface of the balloon 420. The sets of transducer elements can each consist of two elements 460 at an angle of 180 degrees with respect to an axis of the balloon so that they are spaced apart by a distance equal to the diameter of the balloon when the balloon is inflated to a spherical configuration. Other transducer sets may be defined such as sets of three transducers defining the vertices of equilateral triangles or sets of four transducers defining the vertices of regular tetrahedrons. Optionally, all of the transducers 460 may define a single set.

Sets of two transducer elements 460 can be operated to sense opposing walls of a walled area as explained above with respect to the transducers 250 and 260 in FIGS. 2 and 3A-C. Sets of three or more transducers may be defined so that when one transducer of such a set enters a blanking region close to a wall portion that it senses, tracking data from the other transducers in the set is used to control navigation of the probe toward that wall. Optionally, data from multiple sets of transducer elements can be used by the processor 40 (FIG. 1) to generate precise position and tracking information 52 that is displayed to the operator 60.

It will be appreciated, that the term "opposing" as used herein is not intended to be limited to 180 degrees opposite. The "opposing" transducers need only be arranged such that when one transducer of a set enters a blanking region close to a wall portion sensed by that transducer, tracking data from the other transducer(s) in the set is sufficient to control navigation of the probe toward that wall portion. It will be appreciated that it is possible for two transducers of a set to both be sensing a different portion of the same wall. Accordingly, as used herein, the term "opposing wall" includes a different portion of the same wall.

Figure 5A:
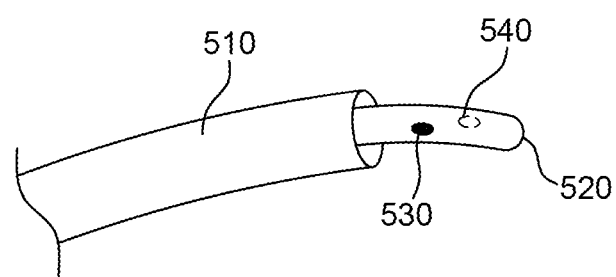
FIGS. 5A and 5B are illustrations of an example probe tool configuration for the distal end of a catheter used in connection with the example medical system of FIG. 1.
Figure 5B:
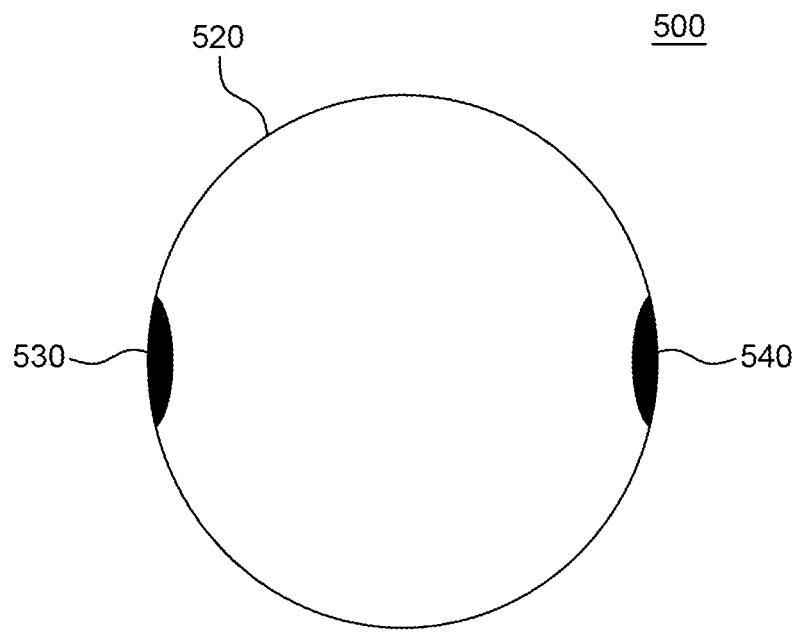

FIGS. 5A and 5B illustrate a further example of use of a set of opposing transducers that can compensate for the blanking region of either transducer. As shown in FIGS. 5A and 5B, a further example configuration of a distal end portion 500 is provided for probe 22. In this example, a tool 520 is extendable from the distal end of a probe sheath 510. In this example, the tool 520 itself includes a first transducer 530 mounted on one side and a second transducer 540 mounted on an opposing side. The opposing transducer elements 530, 540 can be operated to sense opposing walls of a walled area as explained above with respect to the transducers 250 and 260 in FIGS. 2 and 3A-C.

Although embodiments employing one or more 180 degree opposing sets of transducers may be preferred for specific embodiments, variations can be employed within the scope of the invention. Although the geometric, speed and vector computations become more complex when considering transducer data from more than two of transducers disposed 180 degrees from each other, the sets of transducers can comprise transducers at different known angular orientations to one another, as well as transducer sets including more than two transducers, such as referenced above with respect to FIG. 4. The relative angular orientation of each transducer may be taken into account in the calculation of positioning and tracking data that can be used to compensate for any one of the transducers of the set that enters a blanking region where it cannot properly operate.

Other variations and alternatives will be apparent to those skilled in the art and are within the scope of the foregoing disclosure.

What is claimed is:

1. A method of probe navigation within a subject comprising:
    positioning a distal end of a probe in a walled cavity within the subject wherein the distal end includes a balloon having a first and a second opposing transducers mounted thereon where the transducers are coupled with a signal processor that is programmed to:
        cause the first transducer to transmit pulses and provide tracking data based on first transducer pulse echoes, and
        ignore first transducer pulse echoes when the first transducer is within a blanking distance of an object;
    expanding the balloon within the walled cavity to position the transducers at expanded positions relative to the probe and at an expected distance from each other;
    with the transducers at their respective expanded positions:
        sensing a first wall within the walled cavity by the first transducer and an opposing wall within the walled cavity by the second opposing transducer;
        tracking movement of the distal end of the probe towards the first wall using the first transducer and with respect to the opposing wall using the second transducer; and
        moving the distal end of the probe to bring the first transducer into contact with the first wall such that, upon a condition that the distal end of the probe enters a blanking region defined by the blanking distance from the first wall where the signal processor causes the first transducer pulse echoes from the first wall to be ignored, tracking information of the movement of the probe with respect to the opposing wall generated by the second transducer is used to provide tracking of the distal end of the probe relative to the first wall whereby contact with the first wall by the first transducer over the blanking distance is determinable irrespective of the inability of the first transducer to properly sense the first wall.

2. The method of claim 1 wherein the probe includes a catheter and the walled cavity within which distal end of the catheter is positioned is a heart chamber of a living subject and the distal end of the catheter is moved into contact with a wall of the heart chamber.

3. The method of claim 2 wherein positioning and/or tracking information of the distal end of the catheter is displayed, graphically or otherwise, on a display and an operator moves the distal end of the probe based on the displayed information.

4. The method of claim 1 wherein:
the probe includes a catheter that has a lumen configured to allow tool deployment;
a distal end of the catheter includes the balloon having the first and second transducers mounted thereon; and
the second transducer tracks the distal end of the probe's movement away from the opposing wall when the distal end of the probe is moved towards the first wall.

5. The method of claim 4 wherein the balloon includes an array of transducer supporting members and a plurality of transducers provided on each supporting member at selectively defined positions such that the transducers are located at expanded positions relative to the probe and at an expected distance from each other upon expansion of the balloon, the method further comprising:
defining sets of transducers including at least two transducers of different supporting members such that each transducer in a set is configured to sense a different wall portion of the walled cavity;
selecting a set of transducers that includes the first and second transducers; and
with the transducers at their respective expanded positions, using the selected set of transducers to move the distal end of the probe to bring the first transducer to contact the first wall such that upon a condition that the first transducer enters the blanking region defined by the blanking distance from the first wall where the signal processor causes the first transducer pulse echoes from the first wall to be ignored, tracking information of the movement of the probe with respect to the wall portions sensed by the second and any other transducers of the selected set provide tracking of the distal end of the probe relative to the first wall whereby contact with the first wall by the first transducer over the blanking distance is determinable irrespective of the inability of the first transducer to properly sense it.

6. The method of claim 4 wherein:
the walled cavity within which the distal end of the catheter is positioned is a heart chamber of a living subject; and
the distal end of the catheter is moved into contact with a wall of the heart chamber.

7. The method of claim 6 wherein:
positioning and/or tracking information of the distal end of the catheter is displayed on a display; and
an operator moves the distal end of the probe based on the displayed information.

8. The method of claim 1 wherein the first and second transducers are positioned on the balloon at an angle of 180 degrees from each other with respect to an axis of the probe at the expanded positions relative to the probe.

9. The method of claim 1 wherein the balloon includes a third transducer, further comprising:
sensing a wall within the walled cavity by the third transducer;
tracking movement of the distal end of the probe relative to the wall sensed by the third transducer using the third transducer; and
upon a condition that the first transducer enters the blanking region defined by the blanking distance from the first wall with the transducers at their respective expanded positions where the signal processor causes the first transducer pulse echoes from the first wall to be ignored, using tracking information generated by the second and third transducers of the movement of the probe relative to the walls sensed by the second and third transducers respectively to provide tracking of the distal end of the probe relative to the first wall whereby contact with the first wall by the first transducer over the blanking distance is determinable irrespective of the inability of the first transducer to properly sense the first wall.

10. The method of claim 9 wherein the first, second and third transducers are positioned on the balloon positioned equidistance from each other at the extended positions relative to the probe.

11. A probe navigation system for use with a subject:
a control system and associated probe configured to be operated to controllably insert and move a distal end of the probe to and within a walled cavity within the subject;
the distal end of the probe includes a balloon having a first and a second opposing transducers mounted thereon where the transducers are coupled with a signal processor that is programmed to:
cause the first transducer to transmit pulses and provide tracking data based on first transducer pulse echoes, and
ignore first transducer pulse echoes when the first transducer is within a blanking distance of an object;
the balloon being expandable within the walled cavity to position the transducers at expanded positions relative to the probe and at an expected distance from each other;
the first transducer positioned on the probe to sense a first wall within the walled cavity and the second opposing transducer positioned on the probe-to sense an opposing wall within the walled cavity;
upon a condition that the balloon is expanded within the walled cavity to thereby position the transducers at the expanded positions relative to the probe, the control system configured to track movement of the distal end of the probe towards the first wall using the first transducer and with respect to the opposing wall using the second transducer; and
upon a condition that the first transducer enters a blanking region defined by a blanking distance from the first wall with the transducers at their respective expanded positions where the signal processor causes the first transducer pulse echoes from the first wall to be ignored, the control system configured to use information generated by the second transducer of the movement of the probe with respect to the opposing wall to provide tracking of the distal end of the probe towards the first wall whereby contact with the first wall by the first transducer over the blanking distance is determinable irrespective of the inability of the first transducer to properly sense the first wall.

12. The probe navigation system of claim 11 wherein the control system includes a processor coupled with the transducers and configured to calculate the tracking information of the probe movement based on transducer signals, a display coupled with the processor configured to display the tracking information in one or more modes, and an operable probe control device configured to be operated to selectively control the positioning of the distal end of the probe based on the displayed tracking information.

13. The probe navigation system of claim 12 wherein the probe includes a catheter that has a lumen configured to allow tool deployment and wherein a distal end of the catheter includes the balloon having the first and second transducers mounted thereon.

14. The probe navigation system of claim 12 wherein the control system is configured to track movement of the distal end of the probe away from the opposing wall using the second transducer when the probe is moved towards the first wall.

15. The probe navigation system of claim 12 wherein the balloon includes:
- an array of transducer supporting members;
- a plurality of transducers provided on each supporting member at selectively defined positions such that the transducers are located at expanded positions relative to the probe and at an expected distance from each other upon expansion of the balloon whereby the first and second transducers are among the transducers provided on the supporting members;
- the transducers being allocable by the control system into sets for selectively controlling movement of the distal end of the probe such that each transducer in a set is configured to sense a different wall portion of the walled cavity wherein a first set of transducers includes the first and second transducers; and
- the control system configured to control movement of the distal end of the probe using the transducers of the first set such that:

upon a condition that the first transducer enters the blanking region defined by the blanking distance from the first wall with the transducers at their respective expanded positions where the signal processor causes the first transducer pulse echoes from the first wall to be ignored, tracking information of the movement of the probe with respect to the first wall is provided by the second and any other transducers of the first set whereby contact with the first wall by the first transducer over the blanking distance is determinable irrespective of the inability of the first transducer to properly sense it.

16. The probe navigation system of claim 12 wherein the first and second transducers are disposed 180 degrees from each other on the balloon when at the expanded positions relative to the probe.

17. The probe navigation system of claim 15 wherein the first set is defined by three transducers disposed as vertices of an equilateral with respect to each other on the balloon when at the expanded positions relative to the probe.

18. The probe navigation system of claim 15 wherein the first set is defined by four transducers disposed as vertices of a regular tetrahedron with respect to each other on the balloon when at the expanded positions relative to the probe.

19. The probe navigation system of claim 12 wherein the probe includes a catheter that has a lumen configured to allow tool deployment.

20. The probe navigation system of claim 12 wherein the first and second transducers are mounted on the distal end of the probe at an angle of 180 degrees from each other with respect to an axis of the probe when at the expanded positions relative to the probe.

* * * * *

UNITED STATES PATENT AND TRADEMARK OFFICE
CERTIFICATE OF CORRECTION

PATENT NO. : 11,471,219 B2
APPLICATION NO. : 15/680292
DATED : October 18, 2022
INVENTOR(S) : Andres Claudio Altmann It is certified that error appears in the above-identified patent and that said Letters Patent is hereby corrected as shown below:

In the Specification

In Column 1, Line 13, delete "end of on" and insert -- end on --, therefor.

In Column 2, Line 27, delete "invention;" and insert -- invention. --, therefor.

In Column 2, Line 31, delete "is a" and insert -- are a --, therefor.

In Column 5, Line 30, delete "ultra sound transducers" and insert -- ultrasound transducers --, therefor.

In Column 5, Line 59, delete "that is does" and insert -- that it does --, therefor.

In Column 6, Lines 51-52, delete "in unable" and insert -- is unable --, therefor.

In Column 7, Line 34, delete "supporting member pair 470" and insert -- supporting complementary pair 470 --, therefor.

In the Claims

In Column 9, Line 37, in Claim 5, delete "that upon" and insert -- that, upon --, therefor.

Signed and Sealed this
Twelfth Day of September, 2023

Katherine Kelly Vidal
*Director of the United States Patent and Trademark Office*